United States Patent
Parfenov et al.

(10) Patent No.: US 6,365,363 B1
(45) Date of Patent: Apr. 2, 2002

(54) METHOD OF DETERMINING SKIN TISSUE CHOLESTEROL

(75) Inventors: Alexandr Sergeivich Parfenov; Yuri Michaelovich Lopukhin, both of Moscow (RU)

(73) Assignee: IMI International Medical IInnovations, Inc., Mississauga (CA)

( * ) Notice: Subject to any disclaimer, the term of this patent is extended or adjusted under 35 U.S.C. 154(b) by 0 days.

(21) Appl. No.: 09/367,724

(22) PCT Filed: Jan. 26, 1998

(86) PCT No.: PCT/RU98/00010

§ 371 Date: Nov. 10, 1999

§ 102(e) Date: Nov. 10, 1999

(87) PCT Pub. No.: WO98/37424

PCT Pub. Date: Aug. 27, 1998

(30) Foreign Application Priority Data

Feb. 20, 1997 (RU) .......................... 97102570

(51) Int. Cl.[7] .................. C12Q 1/60; C12Q 1/00; C12Q 1/26; C12Q 1/44
(52) U.S. Cl. ............................ 435/11; 435/4; 435/19; 435/25
(58) Field of Search ................. 435/11, 4, 25, 435/19

(56) References Cited

U.S. PATENT DOCUMENTS 4,226,713 A  10/1980  Goldberg .................. 23/230
4,680,259 A * 7/1987  Cumbo et al.
5,587,295 A  12/1996  Lopukhin et al. ............. 435/11

FOREIGN PATENT DOCUMENTS

SU  637097  12/1978
SU  664536  5/1979

OTHER PUBLICATIONS

JP 08248022A (Derwent Acc No 1996–488925). Quantitative analysis of cholesterol peroxide in skin, providing rapid analysis,1996.*

* cited by examiner

Primary Examiner—Ralph Gitomer
Assistant Examiner—Mahreen Chaudhry
(74) Attorney, Agent, or Firm—Shanks & Herbert

(57) ABSTRACT

A method of determining skin tissue cholesterol includes preparing a section of skin surface, applying a dosed amount of an enzyme-containing mixture onto the skin, exposing, evaluating the concentration of cholesterol in a reaction solution and calculating the concentration of skin cholesterol, wherein the area of contact of the skin with the mixture is limited on the section of the skin surface by means of a sealing vessel without a bottom with a base fixed on the skin, a mixture comprising 2.0–2.5 units of cholesteroloxidase, 0.04–0.06% by weight of sodium dezoxycholate, 0.1–0.2.% by weight of 3-(dodecyl-dimethyl-ammonium)-propanesulfonate in a buffer solution with pH=6.8 is used as the mixture, evaluating the concentration of cholesterol in the reaction solution is carried out by measuring the level of hydrogen peroxide. Measurements of the level of hydrogen peroxide may be carried out by immersing an electrochemical sensor or a colorimetric indicator in the reaction solution.

6 Claims, 1 Drawing Sheet

METHOD OF DETERMINING SKIN TISSUE CHOLESTEROL

FIELD OF THE INVENTION

The invention relates to the field of medicine, more exactly to a method of examining the skin with biochemical methods. The invention may also be used in cosmetology, pharmacology, criminalistics, etc., to determine the content of cholesterol, both free and total, in the skin.

BACKGROUND ART

In clinical conditions the determination of cholesterol in the skin makes it possible in a noninvasive manner, i.e. without taking blood samples or biopsy material, to evaluate the level of tissue cholesterol.

A method is known for determining the presence of different chemical substances on the surface of the skin, these substances being in the blood channel of a human or animal (glucose, alcohol, lactate, hypoxanthine). The method includes the subcutaneous administration of an enzyme immobilized on a silicon surface, heating a section of the skin to 38–44° C. and registering a local change in the concentration of oxygen or hydrogen peroxide on the skin by means of an electrochemical sensor (U.S. Pat. No. 4,458,686, A 61 B 5/00, published July 1984).

A drawback of the known method is the complexity of subcutaneous administration of an immobilized enzyme, the formation of hydrogen peroxide directly in tissues, which may result in undesirable consequences (the transition of hemoglobin into methemoglobin)—the development of hypoxia.

A method is known for determining skin cholesterol by taking samples of tissue with subsequent extraction of cholesterol. The method makes it possible to determine not only the amount of total cholesterol, but separately free and esterified (H. Bouissou, M. Th. Pieraggi, M. Julian, Identifying arteriosclerosis and aortic ateromathosis by skin biopsy. Atherosclerosis, v. 19, pp. 449–458).

A development of this method is an extraction method, in accordance with which extraction of cholesterol is carried out without taking a tissue sample directly on a section of live skin. A mixture of ethyl alcohol and ether is used as the extractant. A test tube with the extractant is held against the surface of the skin for several minutes. The lipids which are in the surface layers of the skin dissolve and pass into the extractant solution, after which evaporation of the solvent is carried out and the substances passing into a liquid phase are determined (Yu. M. Lopukhin. The skin and atherosclerosis [a three-drop test]. 1992, Gordon and Breach Science Publishers S.A. UK).

The content of cholesterol in the epidermis reflects the accumulation of cholesterol in the skin and correlates with the content of the latter in the aorta, and also with the area of damage of the aorta in the case of atherosclerosis (Yu. M. Lopykhin. The skin and atherosclerosis [a three-drop test], 1992, Gordon and Breach Science Publishers S.A. UK). Thus, determination of the content of cholesterol in the skin makes it possible to obtain unique information on the state of the tissue pool of cholesterol, and this is extremely important from both the point of view of early diagnosis of atherosclerosis (preclinical state) and for the purpose of monitoring the treatment of patients with atherosclerosis.

In pharmacology, the method of determining cholesterol in the skin makes it possible to carry out evaluation of the effectiveness of drugs which affect both the synthesis of cholesterol in tissues (a group of statins), and its removal from the organism by means of different sorbents.

A drawback of the known method is the necessity of carrying out a biopsy, contact of skin with the solution of extractants, and also the lengthy time necessary to carry out the analysis.

The method most similar to the proposed method is the method of determining skin cholesterol including preparing a section of skin surface, applying onto the skin (or another cholesterol-containing surface) a dosed amount of a solution that is an affino-enzymatic conjugate of a general structure A—C—B, wherein A is a compound capable of linking with cholesterol (affinate), C is a linking bridge or polymer, B is an enzyme providing a color product as a result of conversion of an according substrate. The amount of cholesterol is determined according to the intensity of the transition of the dye to a dyed form (U.S. Pat. No. 5,489,510, A 61 B 10/00, published February 1996—prototype).

Drawbacks of this method are the limited field of use, i.e. the impossibility of determining esterified cholesterol, the low specificity of the analysis, in particular interaction of the conjugate not only with cholesterol, but also with other lipids.

DISCLOSURE OF THE INVENTION

The object to the attainment of which the instant invention is directed is to increase the specificity, simplify and expand the field of utilization of the method, increase the accuracy of determination of cholesterol in the skin of a human and other condensed mediums.

The stated object is attained in a method of determining skin cholesterol, including preparing a section of a surface, applying onto the skin surface a dosed amount of an aqueous solution of an enzyme with addition of a surfactant, exposing, evaluating the concentration of cholesterol in a reaction solution and calculating the concentration of skin cholesterol, in that in accordance with the proposal, after preparing the section of the surface, an area of contact of the skin with the enzyme solution and the surfactant is limited by means of an appliance, the enzyme solution with the surfactant for determination of free tissue cholesterol has the following composition (% by weight):

| | |
|---|---|
| cholesteroloxidase | 2.0–2.5 units |
| sodium dezoxycholate | 0.04–0.06 |
| 3-(dodecyl-dimethyl-ammonium)-<br>-propanesulfonate | 0.1–0.2 |
| phosphate buffer pH 6.8 | balance to 100%, | while in order to determine the total cholesterol, the composition has the following makeup (% by weight);

| | |
|---|---|
| cholesteroloxidase | 2.0–2.5 units |
| cholesterolesterase | 3–5 units |
| sodium dezoxycholate | 0.04–0.06 |
| 3-(dodecyl-dimethyl-ammonium)-<br>-propanesulfonate | 0.1–0.2 |
| phosphate buffer pH 6.8 | balance to 100%, | exposing the solution on the skin is carried out for 2 minutes to determine free cholesterol and for 10 minutes to determine total cholesterol, while evaluation of the concentration of cholesterol is carried out by direct measurement of the concentration of hydrogen peroxide in the reaction solution.

Limitation of the area of contact of the skin with the surfactant solution is carried out using a sealed cuvette without a bottom with a base fixed on the skin.

Cholesteroloxidase, obtained from different sources (Brevibacterium sp., Nocardia erythropolis), is used. The hydrogen peroxide generated during interaction of cholesterol with cholesteroloxidase is determined by means of an electrochemical sensor or by using spectrophotometric equipment.

The cholesteroloxidase catalyzes oxidation of cholesterol with the participation of molecular oxygen and the formation of hydrogen peroxide:

cholesterol+$O_2$=4-cholestine-3-OH+$H_2O_2$

When a mixture of a surfactant—ionic detergent (sodium dezoxycholate [DOC])—in a concentration of 0.04–0.06% and a zwitterion detergent - 3-(dodecyl-dimethyl-ammonium)-propanesulfonate (DAPS) in a concentration of 0.1–0.2% is used, optimum speed and completeness of oxidation of cholesterol are detected. This reaction system makes it possible to enhance the effectiveness of action of cholesteroloxidase as a result of reduction of the inhibiting action of the surfactant and to reduce the consumption of expensive detergents. Such a composition of detergents ensures access to free cholesterol and a high speed of its oxidation. This makes it possible to use relatively low concentrations of cholesteroloxidase in the determination of free cholesterol. When a kinematic variant of measurement is used, only 4–8 nmols per ml of reaction mixture, and during determination according to the final point to carry out complete oxidation of cholesterol in 10 minutes, 20 nmols of enzyme per ml of reaction mixture are sufficient.

Photometric methods make it possible to achieve the lower limit of detecting oxidase substrates of about $10^{-6}$M.

An electrochemical sensor with cholesteroloxidase, immobilized on a collagen membrane, makes it possible to determine the concentration of cholesterol from $10_{-4}$ to 0.08 mM (USSR patent 622424, G 01 N 33/16, 1976. Bertand et al. 1981. Multipurpose electrode with different enzyme bound to collagen films. Analyt. Chim. Acta. V.126, pp. 23–34).

TABLE 1

| DAPS, % | Sodium dezoxycholate (DOC), % | | | | | | | | |
|---|---|---|---|---|---|---|---|---|---|
| | 0 | | 0.02 | | 0.04 | | 0.06 | | 0.08 |
| | V | OD | V | OD | V | OD | V | OD | V | OD |
| 0 | 0 | 0 | 0 | 0 | 0 | 0 | 0 | 0 | 3 | 0.08 |
| 0.10 | 27 | 0.067 | 51 | 0.08 | 47 | 0.071 | 41 | 0.069 | 33 | 0.068 |
| 0.15 | cloudy solution | | 58 | 0.108 | 53 | 0.118 | 41 | 0.109 | 38 | 0.093 |
| 0.20 | cloudy | | 72 | 0.103 | 63 | 0.112 | 51 | 0.108 | 45 | 0.103 |
| 0.25 | cloudy | | 74 | 0.110 | 65 | 0.105 | 53 | 0.108 | 44 | 0.097 |

Data are presented in Table 1 which were obtained during oxidation of free cholesterol contained in a control solution of cholesterol with different ratios of the two indicated detergents. The results are presented in units of optical density (OD) and the speed of reaction of oxidation according to the value of the angle of inclination of the kinetic curve (V).

VARIANTS OF CARRYING OUT THE INVENTION

The method is realized in the following manner. At first a section of the skin on which measurement is to be carried out is rubbed with a tampon moistened with ethyl alcohol. A special appliance is fixed on the prepared section of skin surface—a sealed cuvette without a bottom (FIG. 1), where 1 is a cuvette with a thread for fixing an electrochemical sensor or lid; 2 is a substrate, ensuring fixation of the cuvette and its air-tightness on the skin surface. The cuvette makes it possible to limit the area of skin surface (1 $cm^2$), where the analysis is to be made, and to apply onto that section (FIG. 2) a dosed amount (volume 0. 1 ml) of a solution of a mixture of an enzyme with a surfactant.

Exposition of the solution on the skin is carried out within two minutes. During the exposition of the solution comprising the mixture of enzyme and the surfactant, hydrogen peroxide is generated, the concentration of which is directly proportional to the content of cholesterol. After exposition the solution containing hydrogen peroxide is carried to an electrochemical electrode where measurement of the concentration of the generated hydrogen peroxide takes place.

Figure 3:
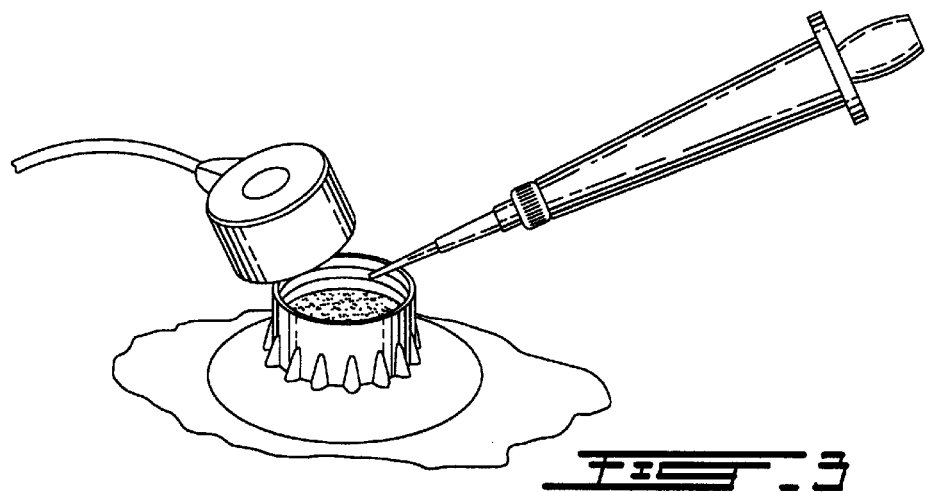
FIG. 3 shows an electrochemical electrode brought into contact with the solution.

A variant of the method is proposed in which an electrochemical electrode is brought into contact with the solution in the cuvette directly on the surface of the skin (FIG. 3).

In the case where a spectrophotometric method of measuring the concentration of hydrogen peroxide is used, a solution comprising hydrogen peroxide is carried into the cuvette of a photometer where the developing system (peroxidase enzyme and substrate). The concentration of the peroxide is determined by the value of the optical density of the solution, which is directly proportional to the concentration of hydrogen peroxide. Determination of the concentration of hydrogen peroxide in a liquid phase with the use of a photometer is preferable in laboratory conditions. Outside the laboratory, for example, in home diagnosis, it is possible to use methods with the use of "dry" chemistry technology. In order to do this colorimetric indicators on paper strips may be used, which make it possible to determine the concentration of hydrogen peroxide in the range of from 0.2 to 20 mg/l that fully covers the necessary range of concentrations.

When working with a colorimetric indicator (strip), the paper strip is immersed in a solution of exposed enzyme and surfactant, which is on the skin surface in a cuvette. After immersion, the change in the color of the strip is evaluated, which is also determined by the concentration of the generated hydrogen peroxide or by means of a color scale or by means of a portable reflective photometer.

Determination of the amount of cholesterol on the skin surface is not only possible according to the amount of hydrogen peroxide generated in the course of the oxidation reaction of cholesterol with an cholesteroloxidase enzyme, but also according to the value of consumption of oxygen in the course of the reaction, and also the value of oxidized cholesterol—cholestenone. The technology of determining hydrogen peroxide is preferable from the point of view of convenience and relative simplicity.

Not only the determination of free, but also of esterified cholesterol is important in diagnosis, since their ratio changes in a number of diseases. Determination of esterified cholesterol makes it possible to carry out the determination of total cholesterol, which is the sum of free and esterified cholesterol. With this object in mind, we carried out enzymic hydrolysis of cholesterol esters with cholesterolesterase enzyme obtained both from tissue of the pancreatic gland and from microbic origin. In order to determine esterified cholesterol on skin surface, a solution of a mixture of enzymes—cholesterolesterase with cholesteroloxidase, and a surfactant was applied on the skin surface. The solution is exposed for 10 minutes after which determination of hydrogen peroxide is carried out with one of the methods indicated above.

EXAMPLE 1

Figure 1:
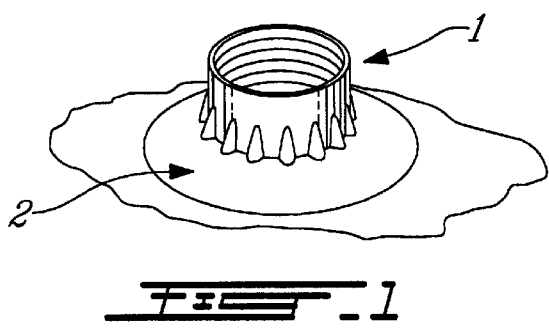
FIG. 1 shows a sealed cuvette without a bottom.
Figure 2:
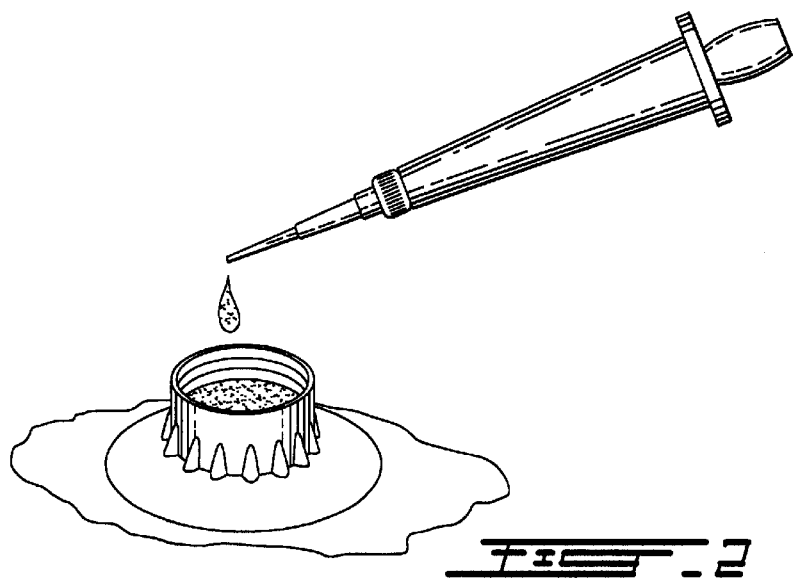
FIG. 2 shows the application of a dosed amount of solution.

Determination of free cholesterol in healthy volunteers by means of an electrochemical sensor. A cuvette shown in FIG. 1 is placed on the skin surface of a palm (tenar region). The cuvette makes it possible to fix a solution of an enzyme and a surfactant with a volume of 0.1 ml on a 1 cm skin surface. At first the skin surface is rubbed with a solution of ethyl alcohol. After the cuvette is set in place, a solution of the following composition (% by weight) is poured therein:

| | |
|---|---|
| cholesteroloxidase | 2.0–2.5 units |
| sodium dezoxycholate | 0.06 |
| 3-(dodecyl-dimethyl-ammonium)--propanesulfonate | 0.2 |
| phosphate buffer pH 6.8 | balance to 100%. |

After incubation of the solution oil the skin surface for two minutes, 0.05 ml of the solution are taken off and carried to the measuring surface of an electrochemical sensor. The result—a current value proportional to the content of the generated hydrogen peroxide, is read after 5 seconds. A recalculation device makes it possible to show on a liquid crystal screen the value of the content of free cholesterol on skin surface expressed either in $\mu$mol/l or in $\mu$g/cm$^2$.

Determination of cholesterol using method (4) makes it possible to detect one, two or three dyed spots. The results of simultaneous conduction of these two tests are presented in Table 2. It is evident that deviations in the content of free cholesterol in the skin with a change by almost two times from 10.1 to 5.5 $\mu$mol/l provide a positive reaction of one cross, while at a cholesterol concentration of 9.3 $\mu$mol/l the fourth test showed a reaction of two positive crosses (++).

TABLE 2

| No. of test | Free cholesterol, $\mu$mol/l | Three-drop test in crosses |
|---|---|---|
| 1 | 10.1 | (+) |
| 2 | 6.8 | (+) |
| 3 | 5.5 | (+) |
| 4 | 9.3 | (++) |
| 5 | 7.1 | (+) |

EXAMPLE 2

Determination of free cholesterol in patients with stenosing atherosclerosis with clinical manifestations of ischemic heart disease (IHD). When the technology described in Example 1 is used, the level of free cholesterol in the skin of patients with IHD varies within the range of from 18.7 to 35.8 $\mu$mol/l (see Table 3).

TABLE 3

| No. of IHD patient | Free cholesterol, $\mu$mol/l | Three-drop test in crosses |
|---|---|---|
| 1 | 22.5 | (++) |
| 2 | 18.7 | (++) |
| 3 | 27.4 | (+++) |
| 4 | 28.7 | (+++) |
| 5 | 31.9 | (+++) |
| 6 | 20.7 | (+++) |
| 7 | 26.3 | (++) |
| 8 | 25.8 | (++) |
| 9 | 35.8 | (+++) |
| 10 | 20.1 | (++) |
| 11 | 25.0 | (++) |
| 12 | 24.9 | (+++) |
| 13 | 29.1 | (++) |
| 14 | 21.1 | (++) |

EXAMPLE 3

Determination of free cholesterol by means of a special paper strip. A cuvette is placed on the skin surface of the palm (tenar region), making it possible to fix a volume of a solution of an enzyme and a surfactant equal to 0.1 ml on a 1 cm$^2$ skin surface. The skin surface is first rubbed with a solution of ethyl alcohol. After the cuvette has been put in place a solution of cholesteroloxidase and a surfactant is poured therein. After incubation for two minutes, a special paper strip is moistened therein. The result of determination of the content of free cholesterol of the skin is calculated by means of a calibration color scale, or according to the reading of a reflective photometer.

EXAMPLE 4

Determination of total cholesterol (the sum of free and esterified) of skin cholesterol. A cuvette is placed on the skin surface of the palm, fixing a predetermined volume of the following solution on the skin surface:

| | |
|---|---|
| cholesteroloxidase | 2.0–2.5 units |
| cholesterolesterase | 3–5 units |
| sodium dezoxycholate | 0.04 |
| 3-(dodecyl-dimethyl-ammonium)--propanesulfonate | 0.1 |
| phosphate buffer pH = 6.8 | balance to 100%. |

After that the cuvette is closed with a special lid, since the time of exposition in that case is 10 minutes and evaporation may take place in that time, which would result in concentration of the solution. On the average, in the control group, the content of total cholesterol exceeds by 10–20% the value of free cholesterol, i.e. the value of esterified cholesterol is 10–20% of the total skin cholesterol.

What is claimed is:

1. A method of determining cholesterol present on skin surface, comprising the steps of:
   a. providing an open-ended vessel having a base;
   b. providing an enzyme solution comprising 2.0 to 2.5 units of cholesterol oxidase, 0.04 to 0.06 weight % of sodium dezoxycholate, and 0.1 to 0.2 weight % of 3-dodecyl-dimethyl-ammonium-propanesulfonate, buffered to a pH of 6.8 in water;
   c. bringing said vessel into contac with the skin surface in a manner such that the base of said vessel sealingly engages the skin surface, thereby delimiting an area of said skin surface within said vessel;

d. adding a predetermined amount of said enzyme solution into said vessel so that said enzyme solution contacts the skin surface over the delimited area thereof;

e. allowing said enzyme solution to remain in contact with the skin surface over the delimited area thereof for a period of time sufficient for the cholesterol oxidase to catalyze oxidation of cholesterol and cause formation of hydrogen peroxide; and, f. measuring the amount of hydrogen peroxide formed in step (e), the amount of hydrogen peroxide measured being indicative of the concentration of skin cholesterol.

2. A method according to claim 1 wherein said enzyme solution further comprises 3 to 5 units of cholesterol esterase.

3. A method according to claim 2, wherein said 3 to 5 units of cholesterol esterase are added to said enzyme solution in said vessel between steps (d) and (e).

4. A method according to claim 1, wherein step (f) is carried out by spectrophotometry after the addition of peroxidase and a substrate to said enzyme solution in said vessel.

5. A method according to claim 1, wherein step (f) is carried out by means of an electrochemical sensor that is immersed into said enzyme solution.

6. A method according to claim 1, wherein step (f) is carried out by means of a colorimetric indicator immersed into said enzyme solution.

\* \* \* \* \*

UNITED STATES PATENT AND TRADEMARK OFFICE
CERTIFICATE OF CORRECTION

PATENT NO.    : 6,365,363 B1
DATED         : April 2, 2002
INVENTOR(S)   : Alexandr Sergeivich Parfenov et al.

It is certified that error appears in the above-identified patent and that said Letters Patent is hereby corrected as shown below:

<u>Title page,</u>
Item [73], Assignee, should read as follows:
-- IMI International Medical Innovations, Inc.
Mississauga, Ontario, Canada --

Signed and Sealed this

Nineteenth Day of August, 2003

JAMES E. ROGAN
*Director of the United States Patent and Trademark Office*